(12) United States Patent
Gesswein et al.

(10) Patent No.: US 6,296,620 B1
(45) Date of Patent: Oct. 2, 2001

(54) POLYMER BLENDS FOR ULTRASONIC CATHETERS

(75) Inventors: Douglas H. Gesswein, Temecula; Wayne E. Cornish, Fallbrook, both of CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/458,591

(22) Filed: Dec. 9, 1999

(51) Int. Cl.⁷ ................................................. A61B 17/20
(52) U.S. Cl. ................................................................ 604/22
(58) Field of Search ............................. 604/264, 523, 604/524, 525, 526, 527, 528, 529, 530

(56) References Cited

U.S. PATENT DOCUMENTS

| | | | |
|---|---|---|---|
| 5,542,917 | 8/1996 | Nita et al. ........................... | 604/22 |
| 5,656,029 | 8/1997 | Imran et al. ......................... | 604/95 |
| 5,797,920 | * 8/1998 | Kim ................................... | 606/108 |
| 5,827,201 | * 10/1998 | Samson et al. ..................... | 600/585 |
| 5,860,963 | * 1/1999 | Azam et al. ........................ | 604/280 |

* cited by examiner

Primary Examiner—Manuel Mendez
(74) Attorney, Agent, or Firm—Heller Ehrman White & McAuliffe LLP

(57) ABSTRACT

The present invention is directed to an ultrasonic catheter for delivering ultrasonic energy to a treatment location within a patient's body. In a preferred embodiment, the catheter has proximal and distal portions, the distal portion having an outer tubular member. The catheter, preferably, the distal outer tubular member, is formed, at least in part, of a polymeric material blend having a flexural modulus of elasticity less than about 150 ksi.

20 Claims, 3 Drawing Sheets

POLYMER BLENDS FOR ULTRASONIC CATHETERS

FIELD OF INVENTION

This invention relates generally to medical devices and more particularly to ultrasonic angioplasty catheters for effecting ultrasonic ablation of occlusive intravascular lesions.

BACKGROUND OF THE INVENTION

Ultrasound transmitting catheters have been utilized to successfully ablate various types of obstructions from blood vessels of humans and animals. Additionally, ultrasound transmitting catheters may be utilized to deliver ultrasonic energy to mammalian blood vessels for the purpose of preventing or reversing vasospasm, as described in U.S. Pat. No. 5,324,255 (Passafaro, et al.).

Particular success has been observed in ablation of atherosclerotic plaque or thromboembolic obstructions from peripheral blood vessels such as the femoral arteries. Successful applications of ultrasonic energy to smaller blood vessels, such as the coronary arteries, necessitates the use of ultrasound transmitting catheters which are sufficiently small and flexible to permit transluminal advancement of such catheter through the tortuous vasculature of the aortic arch and coronary tree. Accordingly, the safety and efficacy of removing obstructions from coronary arteries by way of ultrasound is largely dependent upon the size and flexibility of the ultrasound transmitting catheter(s) employed.

One particular type of ultrasound transmitting catheter which may be utilized to deliver therapeutic ultrasound to an intracorporeal treatment site comprises an elongate flexible catheter body having rigid distal tip or head member inserted into, and affixed thereto with at least one ultrasound transmission member extending longitudinally through the catheter body being coupled to the distal tip or head member, as described in U.S. Pat. No. 5,542,917 (Nita, et al.), and incorporated herein by reference.

Although these devices are of merit, there still exists a need in the art for further invention, development and refinement of ultrasound catheters to provide catheters with improved drilling performance.

SUMMARY OF THE INVENTION

The present invention is directed to an ultrasonic catheter for delivering ultrasonic energy to a treatment location within a patient's body. In a preferred embodiment, the catheter has proximal and distal portions, the distal portion having an outer tubular member.

The catheter, preferably, the distal outer tubular member, is formed, at least in part, of a polymeric material blend having a flexural modulus of elasticity less than about 150 ksi. Preferably, the catheter is formed of a polymeric material blend with a flexural modulus of elasticity ranging from about 40 to about 126 ksi. More preferably, the polymeric material blend has a flexural modulus of elasticity ranging from about 50 to about 60 ksi.

In one embodiment, the polymeric material blend comprises at least one polymeric material and a filler. The filler, preferably, is barium sulfate. The percent (%) weight ratio of the polymeric material to the filler may range from about 60 to about 85 polymer with a corresponding filler ranging from about 40 to about 15. Preferably, the % weight ratio of the polymeric material to the filler is from about 65 to about 75 polymer with a corresponding filler ranging from about 35 to about 25. In a preferred embodiment, the % weight ratio of the polymeric material to the filler is from about 78 to about 83 polymer with a corresponding filler ranging from about 22 to about 17. The polymeric material blend, optionally, may include a coloring agent, such as purple pigment, in quantity sufficient to impart visible color to the blend, preferably, up to about 5 wt. %.

DETAILED DESCRIPTION OF THE INVENTION

Figure 1:
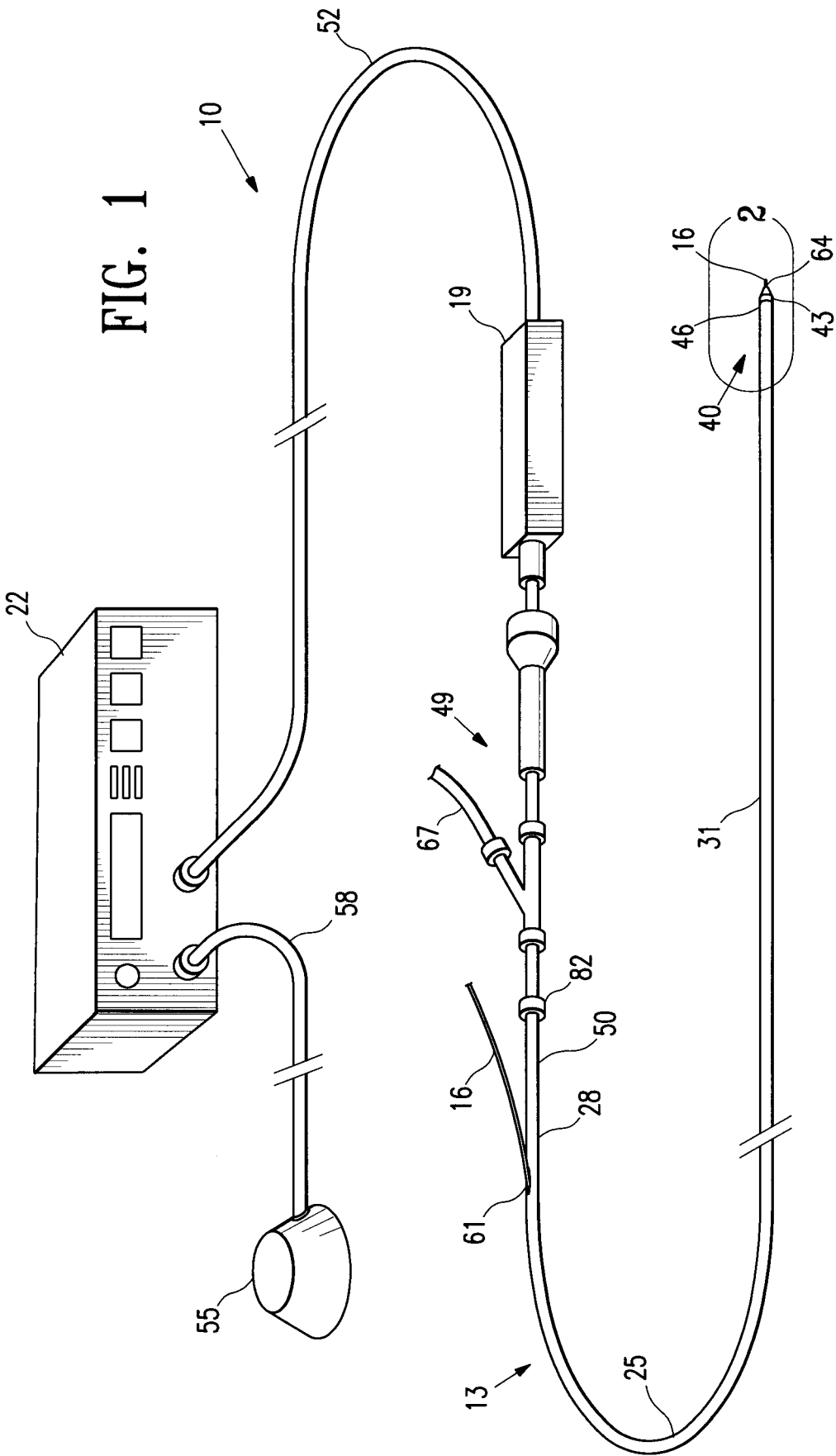
FIG. 1 is a general perspective view of an ultrasound delivering system embodying the present invention.

FIGS. 1 through 4 illustrate features of an ultrasound delivery system 10 including an ultrasound delivery catheter 13 adaptable to receive a guide wire 16, an ultrasound transducer 19, and an electrical signal generator 22.

Figure 2:
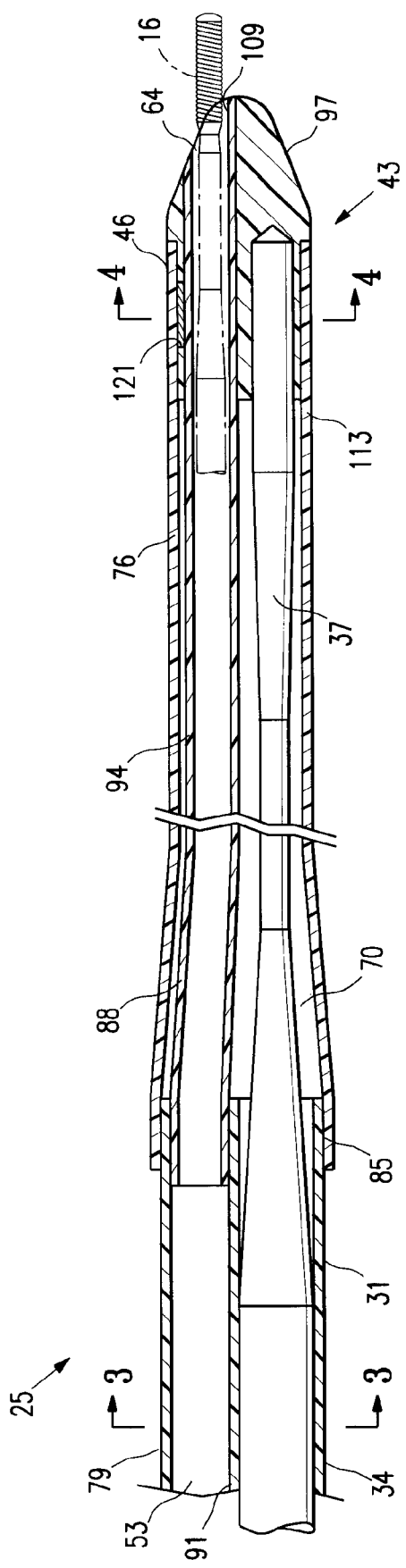
FIG. 2 is a longitudinal sectional view of the catheter in FIG. 1.

The ultrasound delivery catheter 13 comprises an elongate pliable catheter body 25 having a proximal portion 28, a distal portion 31, an outer tubular member 34 (FIG. 2), and at least one ultrasound transmission member 37 extending longitudinally therethrough (FIG. 2). At a distal section 40 of the catheter 13, a distal tip member 43 is mounted on a distal end 46 of the catheter body 25 and the elongate ultrasound transmission member 37 is connected to or in abutment with the distal tip member 43 so as to transmit ultrasonic vibration to the distal portion 31 of the catheter body 25. A proximal connector assembly 49 is positioned at a proximal end 50 of the catheter 13 and is configured and constructed to facilitate operative connection of an proximal end of the ultrasound transmission member 37 to the ultrasound transducer 19 such that ultrasonic energy may be transmitted by the ultrasound transmission member 37, from the ultrasound transducer 19 to the distal end 46 of the catheter 25.

The ultrasound transducer 19 is connected to the electrical signal generator 22 by way of cable 52. An on/off foot pedal switch 55 isconnected to the electrical signal generator 22 by way of a cable 58. By such arrangement, the on/off foot pedal switch 55 may be depressed to cause the signal generator 22 to emit an electrical signal through cable 52 to ultrasound transducer 19. The ultrasound transducer 19 is operative to convert the electrical signal into ultrasound energy at a frequency, and in a pattern which, when transmitted to the distal end 46 of the catheter 25, will effect the intended therapeutic or ablative application.

The catheter 13 shown in FIG. 1 is a "monorail" or "rapid exchange" type of catheter wherein a guide wire passageway extends longitudinally through a distal portion of the catheter body 25, between a first proximal guide wire passage aperture 61 formed in the side wall of the catheter body 25 and a second distal guide wire passage aperture 64 formed in the distal tip member 43 at the distal end 46 of the catheter body 25. By such an arrangement, the guide wire 16 may be longitudinally advanced or retracted through the distal portion of the catheter body, and may be disposed adjacent to an outside of the proximal portion 28 of the catheter body 25.

It will be appreciated that, in an alternative to the "monorail" design shown in FIG. 1, the catheter 13 of the present invention may also be configured as an "over-the-wire" catheter wherein a guide wire lumen extends longitudinally through the catheter body 25 and a guide wire entry/exit side arm (not shown) is formed on the proximal connector assembly 49 such that the guide wire 16 may be inserted through the entire length of the catheter 13, and is insertable/extractable through the side arm.

The proximal connector assembly 49 on the proximal end 50 of the catheter 13 may be configured and constructed in many different ways to accomplish the desired function of operatively coupling the ultrasound transmission member 37 of the catheter 13 to the ultrasound transducer 19, such as that described in U.S. Pat. No. 5,542,917 (Nita, et al.), and incorporated herein by reference.

The connection of the proximal end of the ultrasound transmission member 37 to the ultrasound transducer 19 is accomplished through conventional means, such as that described in Nita, referenced above.

A fluid conduit 67 is formed on the proximal connector assembly 49. The fluid conduit 67 communicates with the catheter 13 via a catheter lumen 70 (FIG. 3) and in this way a radiographic contrast fluid may be introduced through the fluid conduit 67 into the catheter 13. The contrast fluid presents a distinct image of the probe and blockage in an x-ray image, depending on concentration, and allows the treating physician to observe the location of the catheter and probe in the blood vessel while also monitoring the progress of the ultrasonic treatment in destroying the occlusion and improving the flow of blood in the blood vessel. The fluid conduit 67 may also be used for aspiration (suction) of debris from the treatment site through irrigation conduits 73 (FIG. 4) formed in the side wall of the catheter body 25 at its distal portion 31 and being in fluidic communication, as necessary, with the fluid conduit 67. Alternatively, more than one fluid conduit may be provided. For example, one conduit may be used for aspiration while another conduit may be used for contrast fluid.

In many applications, it may be desirable for the catheter 13 to have optimal pliability or flexibility, especially in the distal portion 31 of the catheter body 25, such that the catheter 13 may be inserted into small or tortuous anatomical passageways without crimping of the catheter body or breakage/damage to the ultrasound transmission member 37 as well as providing improved ultrasound transmission properties and ablation performance.

To facilitate this, at least a portion of the outer tubular member 34 of the catheter body 25, is formed at least in part, of a material having a flexural modulus of elasticity less than about 150 ksi, preferably, from about 40 to about 126 ksi, and more preferably, from about 50 to about 60 ksi. Preferably, the material for forming at least a portion of the outer tubular member 34 comprises a polymeric blend comprising at least one polymeric material and a filler, in effective weight ratio to bring about the desired modulus of elasticity. The filler, preferably, is barium sulfate. The at least one polymeric material, preferably, is a polyamide/polyether block copolymer, commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether. The polyamide and polyether blocks are not miscible. Thus the materials are characterized by a two phase structure: one is a thermoplastic region that is primarily polyamide and the other is elastomer region that is rich in polyether. The polyamide segments are semicrystalline at room temperature. The generalized chemical formula for these polyester polymers may be represented by formula I:

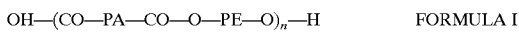

OH—(CO—PA—CO—O—PE—O)$_n$—H         FORMULA I in which PA is a polyamide segment, PE is a polyether segment and the repeating number n is between 5 and 10. The polyamide/polyether polyesters are sold commercially under the PEBAX™ trademark by companies such as Elf Atochem North America Inc. of Philadelphia, Pa. Examples of suitable commercially available polymers are Pebax™ 33 series polymers, with a Shore D hardness value ranging from about 55 to about 75, more preferably from about 60 to about 65; such as Pebax™ 6333.

The ratio of polymer to filler in weight %, is preferably, from about 60 to about 95 wt. % polymer with a corresponding filler wt. % ranging from about 40 to about 5 wt. %, more preferably, from about 65 to about 90 wt. % polymer with a corresponding filler wt. % ranging from about 35 to about 10 wt %, and most preferably, from about 75 to about 85 wt. % polymer with a corresponding filler wt. % ranging from about 25 to about 15 wt %.

The blend, may additionally comprise a coloring agent such as purple pigmentation quantity sufficient to impart visible color to the blend, preferably, up to about 5 wt. %, more preferably up to about 2.5 wt. %.

As shown in the embodiment, features of which are illustrated in FIG. 2, the outer tubular member 34 may comprise of separate distal and proximal outer tubular members, 76 and 79. The proximal outer tubular member 79, at its proximal end, is received within the distal end of the proximal connector assembly 49. A hollow longitudinal bore (not shown), of varying diameter, extends longitudinally through the proximal connector assembly 49, thereby providing a passageway through which the ultrasound transmission member 37 extends from the proximal end of the catheter body 25 to the point at which it is connected to the ultrasound transducer 19.

The proximal outer tubular member 79 at its distal end is received within the proximal end of the distal outer tubular member 76 and is joined thereto by one of many ways known as is in the art, for example, an adhesive layer 85 between the outer surface of the proximal outer tubular member 79 and the inner surface of the outer tubular member 76, where the two surfaces come together.

The catheter body 25 includes a guide wire tubular member 88 extennding through the catheter lumen 70 along, at least part of, the length of the catheter body 25. In the embodiment, features of which are illustrated in FIG. 2, the tubular member 88 comprises at the proximal portion 28 of the catheter body 25 of a tubular member 91 formed integral with the proximal outer tubular member 79 (FIG. 4), and a separate tubular member 94 joined at its proximal end to the distal end of the tubular member 91 and extending distally therefrom to the distal end 46 of the catheter body 25 at distal tip member 43. The tubular members 91 and 94 form a continuous lumen for passage of the guide wire 16 therethrough.

Preferably, the at least part of the catheter body 25 formed of the polymeric blend of the present invention, includes, at least in part, the distal outer tubular member 76.

Figure 5:
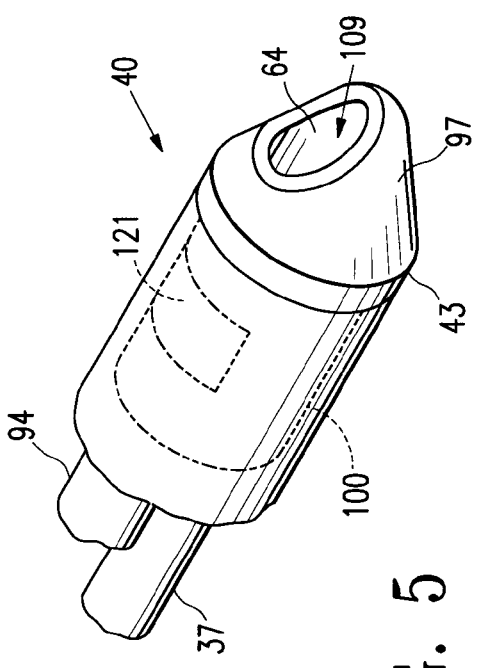
FIG. 5 is an enlarged perspective view of a distal section of the catheter of FIG. 2.

Now referring to FIGS. 5 and 6, the distal section 40 of the catheter 13, will be explained in more detail. The distal tip member 43 of the catheter 13 may be configured and affixed to the distal end 46 of the catheter body 25 in different ways, such as those described in Nita, an example of which is described below.

Figure 4:
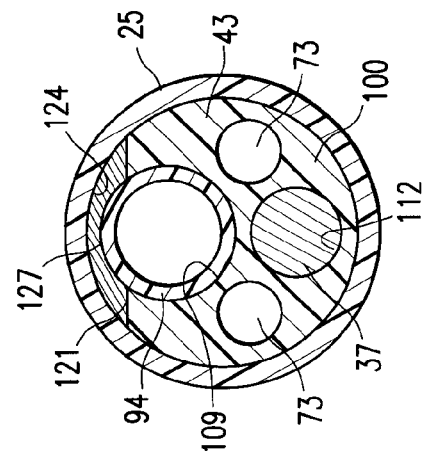
FIG. 4 is a cross sectional view of a proximal portion of the catheter body of FIG. 2 taken along line 4—4.
Figure 3:
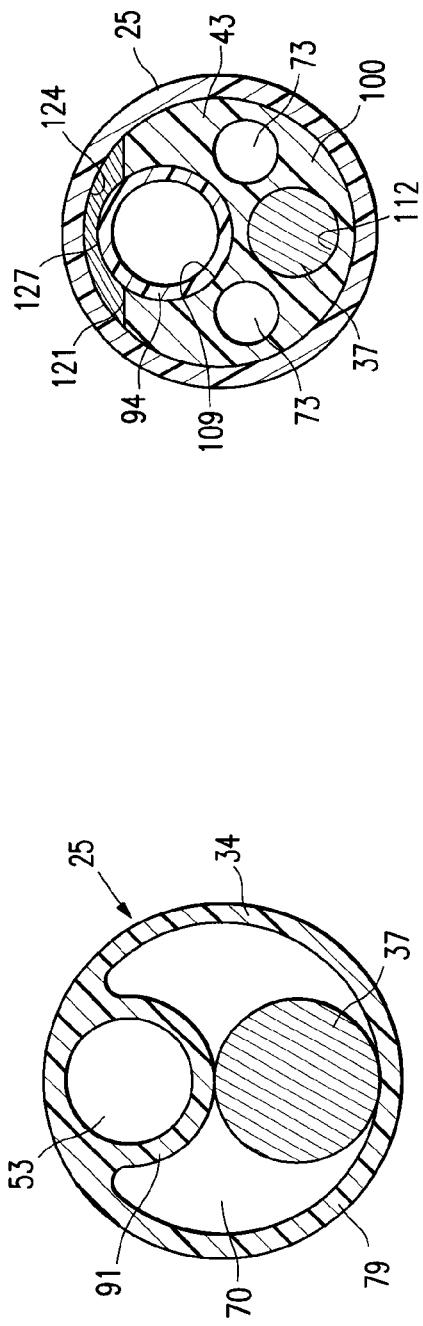
FIG. 3 is a cross sectional view of a distal portion of the catheter body of FIG. 2 taken along line 3—3.

As shown in FIG. 4, the distal tip member 43 comprises a generally conical distal portion 97 and a smaller diameter, generally cylindrical, proximal portion 100. The generally cylindrical proximal portion 100 is sized to be insertable into the distal end 46 of the tubular catheter body 25 such that the distal tip 103 of the tubular catheter body 25 will abut against the annular shoulder 106 of the distal portion 97. A longitudinal guide wire passage bore 109 is formed eccentrically through the entire length of the distal tip member 43 such that the separate guide wire tube 94 may be passed through the catheter lumen 70 and through the guide wire passage bore 109.

The distal end of the guide wire tube 94 is cut flush with the distal face of the distal portion 97 of the distal tip member 43, as shown. When so inserted, the guidewire tube 94 may be affixed or secured to the distal tip member 43 by heat sealing, adhesive or other suitable means.

Also, an ultrasound transmission member receiving bore 112 extends longitudinally into a proximal portion of the distal tip member 43, terminating in a conical or pointed blind end point 115. The ultrasound transmission member receiving bore 112 is formed eccentrically in the distal tip member 43, spaced apart from the location of the guidewire passage bore 109. The ultrasound transmission member receiving bore 112 is sized and configured to receive the distal-most portion of the ultrasound transmission member 37. In the embodiments shown, an extreme distal end 1 18 of the ultrasound transmission member 37 is advanced to a point where it abuts against the decreasing diameter of the blind conical end point 1 15 of the ultrasound transmission member receiving bore 112.

The ultrasound transmission member 37, the guidewire tube 94, and the catheter body 25 may be fixed or engaged to the distal tip member 43 by any suitable means, such as those described in Nita.

Figure 6:
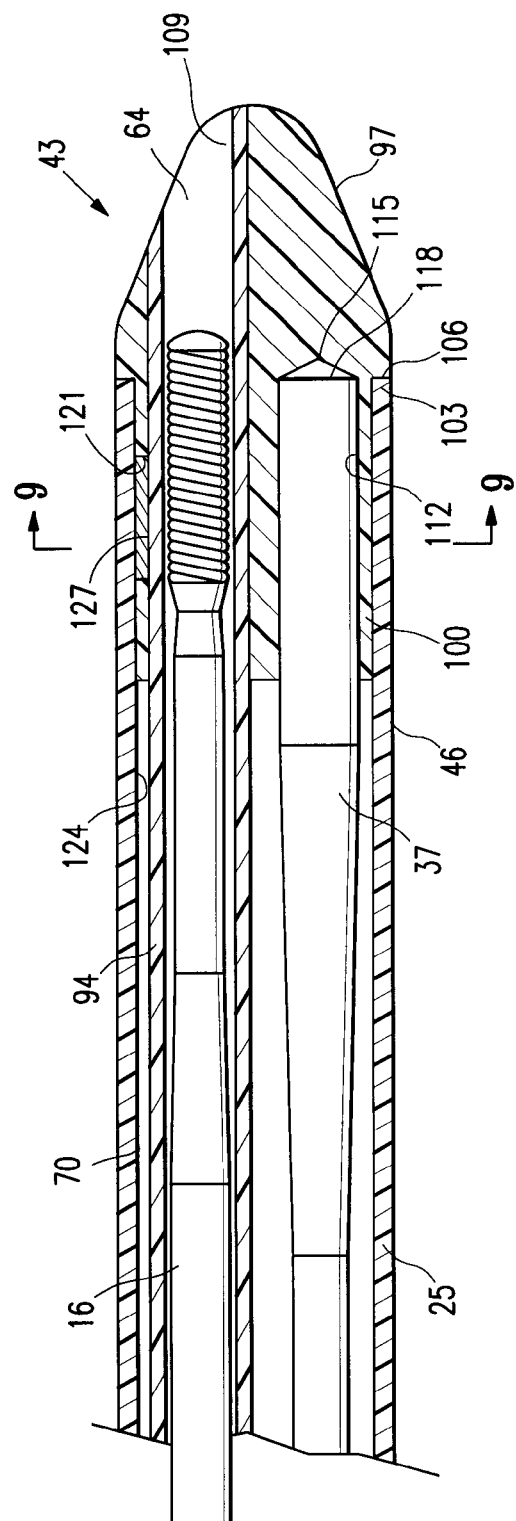
FIG. 6 is a longitudinal sectional view of the distal section of FIG. 5.

For example, as shown in FIG. 6, a three-way bond is formed between the distal end 46 of the catheter body 43, the distal tip member 37 and the guidewire tube 94, by providing an adhesive passage aperture 121 in the proximal portion 100 of the distal tip member 43 such that a quantity of adhesive may be disposed within aperture 121, thereby bonding the inner surface 124 of the tubular catheter body 25 to the outer surface 127 of the guidewire tube 94, while adhesively locking or holding the distal tip member 43 in its desired position within the distal end 46 of the catheter body 25. The adhesive passage aperture 121 may be in the form of a single generally rectangular aperture formed in one side of the proximal portion 100 of the distal tip member 43, extending from the outer surface of the proximal portion 100, into the guidewire passage bore 109 formed therein. A quantity of adhesive may be initially disposed on the outer surface of the proximal portion 100 of the distal tip member 43 and/or within the confines of the aperture 121. Thereafter, the distal tip member 43 is inserted into the distal end 46 of the tubular catheter body 25, and the guidewire tube 94 is passed through the guidewire passage bore 109. The quantity of adhesive which resides or flows through aperture 121, upon curing, will form a three-way adhesive bond between the inner surface 124 of the catheter body 25, the proximal portion 100 of the distal tip member 43 and the outer surface 127 of the guidewire tube 94. Such a three-way bond serves to firmly hold the distal tip member 43 in its desired position while also preventing slippage or release of the guidewire tube 94.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An ultrasonic catheter for delivering ultrasonic energy to a treatment location within a patient's body, the catheter formed, at least in part, of a polymeric material blend having a flexural modulus of elasticity less than about 150 ksi.

2. The catheter of claim 1 wherein the polymeric material blend has a flexural modulus of elasticity ranging from about 40 to about 126 ksi.

3. The catheter of claim 2 wherein the polymeric material blend has a modulus of elasticity ranging from about 50 to about 60 ksi.

4. The catheter of claim 1 wherein the polymeric material blend comprises at least one polymeric material and a filler.

5. The catheter of claim 4 wherein the polymeric material and filler are selected from the group consisting of polyether block amides and barium sulfate, respectively.

6. The catheter of claim 5 wherein the polyether block amide has a Shore D hardness value ranging from about 55 to about 75.

7. An ultrasonic catheter for delivering ultrasonic energy to a treatment location within a patient's body, the catheter having proximal and distal portions, the distal portion having an outer tubular member, the distal outer tubular member formed, at least in part, of a polymeric material blend having a flexural modulus of elasticity less than about 150 ksi.

8. The catheter of claim 7 wherein the polymeric material blend has a flexural modulus of elasticity ranging from about 40 to about 126 ksi.

9. The catheter of claim 8 wherein the polymeric material blend has a modulus of elasticity ranging from about 50 to about 60 ksi.

10. The catheter of any one of claim 7 wherein the polymeric material blend comprises at least one polymeric material and a filler.

11. The catheter of claim 10 wherein the polymeric material and filler are selected from the group consisting of polyether block amides and barium sulfate, respectively.

12. The catheter of claim 11 wherein the polyether block amide has a Shore D hardness value ranging from about 55 to about 75.

13. An ultrasonic catheter for delivering ultrasonic energy to a treatment location within a patient's body, the catheter formed, at least in part, of a polymeric material blend having a flexural modulus of elasticity less than about 150 ksi, wherein the polymeric material blend comprises at least one polymeric material and a filler, wherein the percent weight ratio of the polymeric material to the filler is from about 60 to about 95 polymer with a corresponding filler ranging of about 40 to about 5.

14. The catheter of claim 13 wherein the percent weight ratio of the polymeric material to the filler is from about 65 to about 90 polymer with a corresponding filler ranging from about 35 to about 10.

15. The catheter of claim 13 wherein the percent weight ratio of the polymeric material to the filler is from about 75 to about 85 polymer with a corresponding filler ranging from about 25 to about 15.

16. The catheter of claim 13 wherein the material blend includes up to about 5 wt. % of a colorant.

17. An ultrasonic catheter for delivering ultrasonic energy to a treatment location within a patient's body, the catheter having proximal and distal portions, the distal portion having an outer tubular member, the distal outer tubular member formed, at least in part, of a polymeric material blend having a flexural modulus of elasticity less than about 150 ksi., wherein the polymeric material blend comprises at least one polymeric material and a filler, wherein the percent weight ratio of the polymeric material to the filler is from about 60 to about 95 polymer with a corresponding filler ranging from about 40 to about 5.

18. The catheter of claim 17 wherein the percent weight ratio of the polymeric material to the filler is from about 65 to about 90 polymer with a corresponding filler ranging from about 35 to about 10.

19. The catheter of claim 17 wherein the percent weight ratio of the polymeric material to the filler is from about 75 to about 85 polymer with a corresponding filler ranging from about 25 to about 15.

20. The catheter of claim 17 wherein the material blend includes up to about 5 wt. % of a colorant.

* * * * *